(12) United States Patent
Bonrath et al.

(10) Patent No.: US 6,383,392 B1
(45) Date of Patent: May 7, 2002

(54) PROCESS FOR CONCENTRATING EPIGALLOCATECHIN GALLATE

(75) Inventors: Werner Bonrath, Freiburg (DE); David Carl Burdick, Binningen (CH); Peter Schirg, Badenweiler; Andreas Thum, Ulm, both of (DE)

(73) Assignee: Roche Vitamins, Inc., Parsippany, NJ (US)

( * ) Notice: Subject to any disclaimer, the term of this patent is extended or adjusted under 35 U.S.C. 154(b) by 0 days.

(21) Appl. No.: 09/709,123

(22) Filed: Nov. 8, 2000

(30) Foreign Application Priority Data

Nov. 16, 1999 (EP) .............................. 99122753

(51) Int. Cl.$^7$ .............................. B01D 61/00
(52) U.S. Cl. .................. 210/652; 210/650; 210/651; 426/271; 426/330.3; 426/425
(58) Field of Search .............................. 210/652, 651, 210/805, 195.2, 650; 426/271, 330.3, 425

(56) References Cited

U.S. PATENT DOCUMENTS

| | | | |
|---|---|---|---|
| 5,587,083 A | * | 12/1996 | Twardowski |
| 5,879,733 A | | 3/1999 | Ekanayake et al. |
| 6,068,862 A | * | 5/2000 | Ishihara et al. |
| 6,268,009 B1 | * | 7/2001 | Ekanayake et al. |

FOREIGN PATENT DOCUMENTS

WO    WO 99/08693    2/1999

OTHER PUBLICATIONS

Derwent English language abstract of JP 06256201 (1994).
Derwent English language abstract of JP 06116258 (1994).
Derwent English language abstract of JP 02184626 (1990).
Derwent English language abstract of JP 01299224 (1990).
Derwent English language abstract of JP 62030711 (1987).

* cited by examiner

Primary Examiner—Ana Fortuna
(74) Attorney, Agent, or Firm—Bryan Cave, LLP

(57) ABSTRACT

The present invention is a process for concentrating aqueous epigallocatechin gallate (EGCG) solutions by feeding an aqueous EGCG solution to at least one membrane module under pressure to provide a permeate purge and a retentate return so that in the latter the concentration of EGCG is increased. The permeate purge and the retentate return are then collected.

13 Claims, 1 Drawing Sheet

$V_0$   feed and/or concentrate solution
$V_p$   permeate purge
$V_r$   retentate return ① storage vessel for concentrate and/or feed solution
② pump
③ membrane module
④ permeate vessel

| | |
|---|---|
| $V_0$ | feed and/or concentrate solution |
| $V_p$ | permeate purge |
| $V_r$ | retentate return |

| | |
|---|---|
| ① | storage vessel for concentrate and/or feed solution |
| ② | pump |
| ③ | membrane module |
| ④ | permeate vessel |

PROCESS FOR CONCENTRATING EPIGALLOCATECHIN GALLATE

FIELD OF THE INVENTION

The present invention relates to a process for concentrating aqueous epigallocatechin gallate (hereinafter abbreviated to EGCG) solutions. In particular the invention relates to a process for concentrating aqueous EGCG solutions using selective nanofiltration or reversed osmosis membranes (herein abbreviated to membrane).

BACKGROUND OF THE INVENTION

Ekanayake et al., U.S. Pat. No. 5,879,733 ("Ekanayake '733") describes a process for the preparation of green tea extract having improved clarity and color. These extracts are obtained by treating an aqueous green tea extract with an amount of a food grade cation exchange resin effective to remove metal cations present in the extract. The extract treated with a cation exchange resin is then contacted with a nanofiltration membrane to remove the higher molecular weight materials such as e.g. pectins, proteins, chlorophyll and oxidation products.

The nanofiltration membranes described in Ekanayake '733 are made from polymers having a molecular weight cut off from about 700 to about 5000 Daltons (corresponding to pore sizes in the range of from about 17 to about 40 Angstroms). Polymers such as cellulose acetates, polysulfones, and polyvinylidenefluorides are used for making these nanofiltration membranes. Especially disclosed is the use of an OSMO SP-12 nanofiltration membrane (made by Osmonics, Inc. of Minnetonka, Minn.). The cellulose acetate polymer from which the membrane is made has a molecular weight cut off of 1000 Daltons (corresponding to a pore size of about 20 Angstroms). By use of the membrane, the tea catechins, which have a molecular size smaller than the pore diameter of the membrane pass through the membrane together with water, while the higher molecular weight materials are rejected by the membrane.

Ekanayake '733, however, does not disclose a membrane which is suitable to concentrate aqueous EGCG solutions. Thus, there is still a need to find a membrane that has both a high retention rate of EGCG, and is able to maintain an acceptable flow rate of the permeate stream.

SUMMARY OF THE INVENTION

One embodiment of the invention is a process for concentrating an aqueous epigallocatechin gallate (EGCG) solution. This process includes feeding an aqueous EGCG solution having a dissolved solids content of about 0.03 wt % to about 10 wt % to at least one membrane module under a pressure of about 5 bar to about 100 bar to provide a permeate purge and a retentate return wherein the concentration of EGCG is increased in the retentate return relative to the concentration in the feed solution and whereby the membrane is characterized by a retention coefficient for EGCG of over 90%, collecting the permeate purge, and collecting the retentate return.

DETAILED DESCRIPTION OF THE INVENTION

Figure 1:
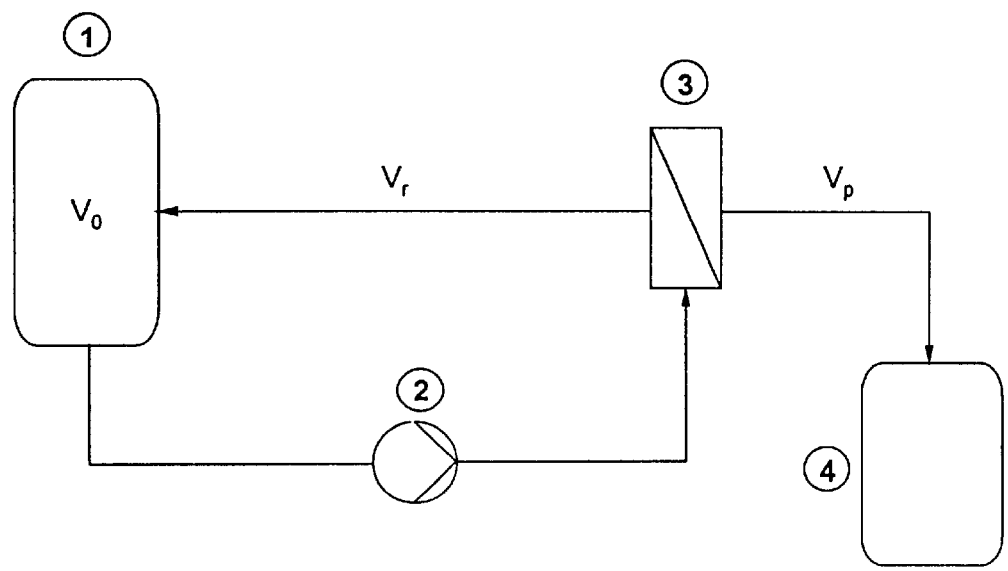
FIG. 1 is a schematic representation of a single stage membrane nanofiltration device according to the present invention.

The present invention relates to a multiple step process for concentrating aqueous epigallocatechin gallate (EGCG) solutions, which process may be performed at least partially batchwise or continuously, and includes the following steps:

a) feeding an aqueous EGCG solution having a dissolved solids content of about 0.03 wt % to about 10 wt % to at least one membrane module under a pressure of about 5 bar to about 100 bar to provide a permeate purge and a retentate return wherein the concentration of EGCG is increased in the retentate return relative to the concentration in the feed solution and whereby the membrane is characterized by a retention coefficient for EGCG over 90%;

b) collecting the permeate purge;

c) collecting the retentate return;

d) optionally recycling the retentate return back to the membrane;

e) optionally concentrating the retentate return of steps c) and/or d); and f) optionally concentrating the permeate purge of step b).

The requirements on the membrane used are: a retention coefficient for EGCG over 90%, a permeate flow rate over 5 l m$^2$ h, a retention coefficient for an optionally added organic solvent and for any impurities present at less than 50%.

Membranes are generally characterized in a defined solvent-membrane-system by the retention coefficient R and the permeate flow rate $J_v$. With regard to the concentration of an aqueous EGCG solution, the retention coefficient R is defined as $R=100\times(1-C_p/C_k)$, wherein $C_p$ is the concentration of EGCG in the permeate and $C_k$ is the concentration of EGCG in the retentate return. The permeate flow is a function of the osmotic pressure, which is caused by all dissolved molecules (e.g. EGCG and organic solvent) in the concentrate. The permeate flow $J_v$ is defined as $J_v=A\times(\Delta P-\Delta \pi)$, wherein A is a membrane constant in $1 l/m^2$ h bar, $\Delta P$ is the transmembrane difference of the pressure, $\Delta \pi$ is the transmembrane difference of the osmotic pressure.

An example for a suitable membrane is the membrane DESAL-5 which is commercially available from OSMONICS/DESAL, Vista, Calif. The DESAL-5 membrane permits concentration of EGCG in a range up to 200 fold.

A preferred pressure range for the membrane is from about 10 bar to about 100 bar, more preferably from about 20 bar to about 35 bar.

The process of the invention may be operated at any suitable and desired temperature selected from about 10° C. to about 60° C.

The term "aqueous EGCG solution" as used herein means a solution of EGCG in a mixture of water and optionally an organic solvent. The solvent or the solvent mixture contains about 70 vol % to about 100 vol %, preferably about 90 vol % of water and about 0 vol % to about 30 vol %, preferably about 10 vol % of an organic solvent. The organic solvent is preferably methanol, ethanol, isopropanol or acetone. The initial concentration of EGCG in the solution is about 0.05 wt % to about to about 10 wt %, preferably about 0.05 wt % to about 2 wt %.

In the present process, the starting material is a green tea extract which can be prepared by methods known in the art e.g. by extracting green tea leaves. Tea extract powders are also commercially available e.g. from Highyin Biological Products Co., Guiyating, China.

EGCG is separated from tea polyphenols present in such extracts by chromatography e.g. as described in the European Patent Application 99116032.6, which discloses a process for producing EGCG according to the following steps:

a) providing a green tea extract;

b) subjecting the green tea extract to a chromatography on a macroporous polar resin at a temperature in the range of about 30° C. to about 80° C.;

c) eluting EGCG from the macroporous polar resin with a polar elution solvent at a temperature in the range of about 30° C. to about 80° C. and at a pressure in the range of about 0.1 bar to about 50 bar;

d) optionally concentrating the eluate of step c);

e) optionally regenerating the macroporous polar resin by desorbing the remaining catechins; and f) optionally concentrating the desorbed catechins of step e).

The process of the present invention will now be set forth in greater detail with reference to FIG. 1. The process is carried out with a device that includes a feed solution vessel (1) connected to a membrane module (3) by a feed conduit through a high pressure pump (2). Module (3) includes a spiral wound type or a flat sheet type module containing the filtration membrane. The permeate purge conduit $V_p$ is connected to a permeate vessel (4). The return conduit $V_r$ is used to recycle the retentate return to vessel (1). A spiral wound module is preferred.

In operation, an aqueous feed solution containing EGCG is passed to module (3) under a pressure of about 5 to about 100 bar by a pump (2). Exiting through $V_p$ is the permeate purge conduit containing water and optionally an organic solvent. Exiting through conduit $V_r$ is the retentate return containing EGCG, which does not pass through the membrane.

For the process depicted in FIG. 1, the retentate return may be sent to the membrane process again, in one or more cycles, in either a batch or a multiple step process (additional concentration of the permeate purge) or as a continuous process.

The following examples are provided to further illustrate the process of the present invention. These examples are illustrative only and are not intended to limit the scope of the invention in any way.

EXAMPLES

Example 1
Preparation of the Starting Material

A chromatography column was filled with 2.2 kg of Amberlite® XAD-7 resin. 50 g green tea extract from Highyin Biological Products Co., Guiyang, China were dissolved in 50 ml deionized water and the obtained solution was adsorbed onto the top of the column at 60° C. and subsequently eluted at 60° C. under an argon atmosphere by an eluent flow of 0.1 l/min. The eluent was a mixture of water/isopropanol (ratio 9:1 by volume). The eluent was degassed and kept under an argon atmosphere prior to use. Three main fractions were obtained containing:

a) 10.0 g EGCG in 10.3 l solution (0.97 g EGCG/l);

b) 5.2 g EGCG in 10.4 l solution (0.50 g EGCG/l); and c) 1.3 g EGCG in 5.6 l solution (0.23 g EGCG/l).

The amount of EGCG was determined by HPLC analysis. Solvents containing specific amounts of EGCG were used as external standards to quantitatively determine the amount of EGCG by HPLC in the above fractions. The fractions were combined, resulting in a feed solution containing 0.63 g EGCG/l water/isopropanol 9/1.

Example 2a
Concentrating the EGCG Solution in a Spiral Wound Membrane Module

Storage vessel (1) was filled with the feed solution of Example 1. The starting volume of the feed solution was 6 l. The rest of the feed solution was added to the membrane module in 2 l-portions. When 2 l permeate were obtained, the solution was passed at ambient temperature through the membrane module (dead volume about 2 l) having a spiral wound membrane element DESAL DL 2540 F containing a DESAL 5 DL membrane. The permeate flow rate was initially 12.2 l/m² h and at the end 6.8 l/m² h. The pressure across the membrane was kept constant at 31 bar. The membrane surface was 2.5 m². The retentate return was returned to vessel (1). 26.3 l feed solution containing 0.63 g EGCG/l were concentrated to 2.06 l. The concentrate was found to have a minimum of 15.6 g EGCG; with a minimum yield of EGCG of 95%. No EGCG could be detected by HPLC in the permeate purge (the limit of detection was about 0.001 mg/ml). The retention coefficient was therefore about 99.99. The concentration factor was about 13.

Example 2b
Concentrating the EGCG Solution in a Flat Sheet Membrane Module

A flat sheet membrane module with about 0.1 l dead volume was used for further concentration of the concentrate obtained in Example 2a.

Storage vessel (1) was filled with the feed solution of Example 2a. The starting Volume of the feed solution was 0.6 l. The rest of the feed solution was added continuously under nitrogen purge until 14.7 g dissolved EGCG were added. The solution was passed at ambient temperature through the membrane module having a flat sheet membrane element DESAL DL 5. The permeate flow rate was initially 16 l/m² h and at the end 3.8 l/m² h. The pressure across the membrane was kept constant at 43 bar. The membrane surface was 0.0028 m². The retentate return was returned to vessel (1) and concentrated to an end volume of 126 ml. The concentrate was found to have a minimum of 14.2 g of EGCG; with a minimum yield of 97%. Traces of EGCG were detected by HPLC in the permeate purge (the limit of quantification was about 0.01 mg/ml). The retention coefficient was therefore about 99.99. The concentration factor was about 16.

Example 3

A feed solution containing 0.98 g EGCG/l water/isopropanol 9/1 was concentrated in a flat sheet membrane module at 35 bar and ambient temperature as described in Example 2b. The retention coefficient was 99.8.

Example 4

A feed solution containing 0.98 g EGCG/l water/isopropanol 9/1 (v/v) was concentrated in a flat sheet membrane module at 35 bar and ambient temperature using the following commercially available membranes. The NITTO membranes are available from Nitto Denko, Japan. The membrane surface was 0.0028 m². The following table shows the results, also including the result of Example 3.

| Membrane | Permeate flow rate (beginning) l/m² h | Retention (beginning) % | Permeate flow rate (end) l/m² h | retention (end) % |
|---|---|---|---|---|
| NITTO 7250 NF | 19 | 93.8 | 8 (after 6.5 h) | 96.9 |
| DESAL 5 DL NF | 22 | >99.1 | 10 (after 6.5 h) | >99.8 |

-continued

| Membrane | Permeate flow rate (beginning) l/m² h | Retention (beginning) % | Permeate flow rate (end) l/m² h | retention (end) % |
|---|---|---|---|---|
| NITTO 7450 NF | 32 | 95.0 | 10 (after 7 h) | 91.1 |
| DESAL YK NF | 23 | 88.0 | 8 (after 7 h) | 86.3 |

The above table clearly shows that the nanofiltration membrane DESAL 5 DL NF achieves an unexpectedly high retention of EGCG, while maintaining an acceptable flow rate of the feed solution to be filtered.

The invention being thus described, it will be obvious that the same may be varied in many ways. Such variations are not to be regarded as a departure from the spirit and scope of the invention and all such modifications are intended to be included within the scope of the following claims.

What is claimed is:

1. A process for concentrating an aqueous epigallocatechin gallate (EGCG) solution which process comprises:
    a) feeding an aqueous EGCG solution having a dissolved solids content of about 0.03 wt % to about 10 wt % to at least one membrane module under a pressure of about 5 bar to about 100 bar to provide a permeate purge and a retentate return wherein the concentration of EGCG is increased in the retentate return relative to the concentration in the feed solution and whereby the membrane is characterized by a retention coefficient for EGCG of over 90%;
    b) collecting the permeate purge; and
    c) collecting the retentate return.

2. A process according to claim 1 further comprising recycling the retentate return back to the membrane module.

3. A process according to claim 2 further comprising concentrating the retentate return from the membrane module and/or from the retentate return of step c).

4. A process according to claim 3 further comprising concentrating the permeate purge of step b).

5. A process according to claim 1 wherein the membrane module is a spiral wound membrane element containing a membrane having a retention coefficient for EGCG of over 90%, a permeate flow rate over 5 l/m² h, and a retention coefficient for an organic solvent and for any impurities present therein of less than 50%.

6. A process according to claim 1 wherein the pressure range for the membrane is from about 10 bar to about 100 bar.

7. A process according to claim 1 wherein the pressure range for the membrane is from about 20 bar to about 35 bar.

8. A process according to claim 1 wherein the process is operated at a temperature from about 10° C. to about 60° C.

9. A process according to claim 1 wherein the aqueous EGCG solution comprises EGCG in water.

10. A process according to claim 9 wherein the aqueous EGCG solution further comprises an organic solvent in admixture with the water.

11. A process according to claim 10, wherein the mixture of water and organic solvent comprises about 70 vol % to about 100 vol % water, and about 0 vol % to about 30 vol % organic solvent.

12. A process according to claim 11 wherein the mixture comprises about 90% water and about 10% organic solvent.

13. A process according to claim 11, wherein the organic solvent is selected from the group consisting of methanol, ethanol, isopropanol, acetone, and mixtures thereof.

* * * * *

UNITED STATES PATENT AND TRADEMARK OFFICE
CERTIFICATE OF CORRECTION

PATENT NO. : 6,383,392 B1
DATED : May 7, 2002
INVENTOR(S) : Werner Bonrath et al.

It is certified that error appears in the above-identified patent and that said Letters Patent is hereby corrected as shown below:

Column 6,
Line 19, please change "10° C." to -- 10° C --.

Signed and Sealed this

Tenth Day of September, 2002

Attest:

JAMES E. ROGAN
Attesting Officer  Director of the United States Patent and Trademark Office